United States Patent [19]
Robinson

[11] Patent Number: 5,739,279
[45] Date of Patent: Apr. 14, 1998

[54] PEPTIDYL 4-AMINO-2,2-DIFLUORO-3-OXO-1,6-HEXANEDIOIC ACID DERIVATIVES AS ANTIINFLAMMATORY AGENTS

[75] Inventor: Ralph Pelton Robinson, Ledyard, Conn.

[73] Assignee: Pfizer Inc., New York, N.Y.

[21] Appl. No.: 373,278

[22] PCT Filed: Apr. 21, 1993

[86] PCT No.: PCT/US93/03589

§ 371 Date: Jan. 26, 1995

§ 102(e) Date: Jan. 26, 1995

[87] PCT Pub. No.: WO94/03480

PCT Pub. Date: Feb. 17, 1994

Related U.S. Application Data

[63] Continuation of Ser. No. 922,889, Jul. 31, 1992, abandoned.

[51] Int. Cl.$^6$ .................................................. A61K 38/08
[52] U.S. Cl. ................................ 530/330; 514/17
[58] Field of Search ........................ 530/330, 331; 514/18, 19

[56] References Cited

FOREIGN PATENT DOCUMENTS

| 195212 | 9/1986 | European Pat. Off. . |
| 9115577 | 10/1991 | WIPO . |

OTHER PUBLICATIONS

R. P. Robinson and K. M. Donahue, J. O. Chem., 1992, 57, No. 26, pp. 7309–7314.
Doherty, A. M., et al., J. Med. Chem., 1992, 35, pp. 2–14.
Thaisrivongs, S., et al., J. Med. Chem., 1985, 28, pp. 1553–1555.
Thaisrivongs, S., et al.., J. Med. Chem., 1986, 29, pp. 2080–2087.
Fearon, K., et al., J. Med. Chem., 1987, 30, pp. 1617–1622.

*Primary Examiner*—David Luxton
*Attorney, Agent, or Firm*—Peter C. Richardson; Gregg C. Benson

[57] ABSTRACT

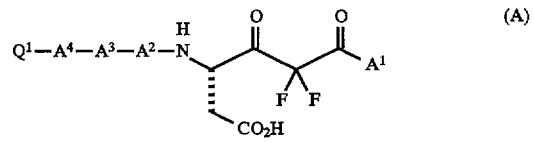

This invention relates to compounds of formula (A) which are derivatives of 4-amino-2,2-difluoro-3-oxo-1,6-hexanedioic acid and their pharmaceutically acceptable base salts. These derivatives and salts thereof are useful for inhibiting interleukin 1β converting enzyme and for treating inflammatory conditions in mammals. The invention also claims three (3) intermediates which are useful for the preparation of said derivatives and salts.

12 Claims, No Drawings

PEPTIDYL 4-AMINO-2,2-DIFLUORO-3-OXO-1,6-HEXANEDIOIC ACID DERIVATIVES AS ANTIINFLAMMATORY AGENTS

CROSS REFERENCE TO RELATED APPLICATIONS

This application is the national stage of International Application No. PCT/US93/03589, filed Apr. 21, 1993, designating, inter alia, the United States which is a continuation of U.S. application Ser. No. 07/922,889, filed Jul. 31, 1992, now abandoned.

BACKGROUND OF THE INVENTION

This invention is concerned with new antiinflammatory agents. In particular, this invention relates to compounds which are derivatives of 4-amino-2,2-difluoro-8-oxo-1,6-hexanedioic acid; to the pharmaceutically acceptable base salts of such derivatives; to methods of using such derivatives in inhibiting interleukin 1β converting enzyme (ICE) and for treating inflammatory conditions in mammals, especially man; and to pharmaceutical compositions useful therefor.

Current therapies for arthritis are severely limited by the side effects of available drugs and their ineffectiveness beyond treatment for disease symptoms. The most widely used drugs are agents (the non-steroidal antiinflammatory drugs, NSAIDS) which inhibit the cyolooxygenase pathway of arachidonic acid metabolism. While these compounds are effective in controlling the symptoms of arthritis, they are not disease remittive. Furthermore, cyclooxygenase inhibition is invariably associated with the major side-effect of NSAID therapy, gastrointestinal irritation. Steroids are used in the more severe cases of arthritis and are very effective. However, long term therapy using steroids is seldomly tolerable. Second line antiinflammatory agents such as gold, penicillamine, chloroquine and methotrexate are also beset with side effect issues which severely limit their general utility.

Interleukin-1 (IL-1) has been strongly implicated as a key mediator of tissue damage in osteo- and rheumatoid arthritis. Lowering levels of IL-1 in a diseased joint would be expected to halt continued degeneration and perhaps allow joint repair to take place. One approach to reducing levels of IL-1 is to block the generation of mature IL-1β from its biologically inactive precursor, pro-IL-1β, by inhibition of the interleukin-1β converting enzyme (ICE). This invention relates to a novel series of compounds which inhibit ICE. The compounds should act as disease remittive antiinflammatory agents and are not expected to elicit the side effects associated with NSAID therapy (due to cyclooxygenase inhibition), steroids or other treatments currently in use.

Peptidyl derivatives containing difluorostatone are described in: S. Thaisrivongs et al., J. Med. Chem., 1986, 29, 2080–2087 and K. Fearon et al., J. Med. Chem., 1987, 30, 1617–1622.

SUMMARY OF THE INVENTION

This invention is concerned with new compounds which are useful for the treatment of diseases associated with elevated levels of interleukin-1 (IL-1). The compounds block the formation of biologically active mature IL-1β from its precursor pro-IL-1β by inhibiting interleukin 1β converting enzyme (ICE).

The compounds of the present invention and their pharmaceutically acceptable salts are of the formula A

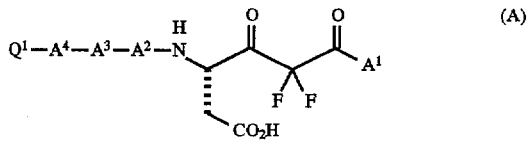

and the pharmaceutically acceptable base salts thereof wherein $A^1$ is L-Pro—$NR^1R^2$ or —$NR^1R^2$, where $R^1$ and $R^2$ are independently selected from the group consisting of hydrogen, $C_1$–$C_6$ alkyl and benzyl; or $R^1$ and $R^2$ are taken together with the nitrogen to which they are attached and form

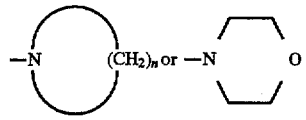

wherein n is an integer from 2 to 6;

$A^2$ is selected from the group consisting of L-His, L-Cys, L-Cys(Me), L-Phe, L-Phe-$R^3$, L-Val, L-Ala, L-Ile, L-Leu and L-Tyr;

$A^3$ is selected from the group consisting of L-Val, L-Leu, L-Ile, L-Tyr, L-Phe and L-Phe- $R^3$;

$A^4$ is selected from the group consisting of a covalent bond, L-Phe, L-Phe-$R^3$, L-Tyr, and L-Leu;

wherein $R^3$ is attached to the aromatic ring of the phenylalanine and for each occurrence is selected from the group consisting of $C_1$–$C_6$ alkyl, $C_1$–$C_6$ alkoxy, benzyl, fluoro, trifluoromethyl and chloro; and $Q^1$ is selected from the group consisting of t-butoxycarbonyl, benzyloxycarbonyl, $R^4CO$ and phenylcarbonyl, wherein $R^4$ is hydrogen, $C_1$–$C_6$ alkyl or benzyl.

The abbreviations used to denote the amino acids are well known and standard in the art and are as follows: Ala, alanine; Pro, proline; His, histidine; Cys, cystine; Cys (Me), methylcystine; Phe, phenylalanine; Val, valine; Ile, isoleucine; Leu, leucine; and Tyr, tyrosine.

A preferred group of compounds have the formula (A) wherein $A^1$ is

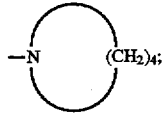

$A^2$ is L-Phe, L-Val, L-Ala, L-Ile or L-Leu; $A^3$ is L-Val; $A^4$ is a covalent bond or L-Tyr, and $Q^1$ is t-butoxycarbonyl.

A more preferred group of compounds have the formula (A) wherein $A^1$, $A^3$, $A^4$ and $Q^1$ are the same as the preferred group of compounds and $A^2$ is L-Ala.

The invention provides a pharmaceutical composition comprising a compound of the formula (A), or a pharmaceutically acceptable base salt thereof, together with a pharmaceutically acceptable diluent or carrier.

The invention also provides a method of inhibiting interleukin 1β converting enzyme (ICE) which comprises administering an effective amount of a compound of the formula (A) or pharmaceutically acceptable base salt thereof, or a pharmaceutical composition as defined above.

The invention further provides a method of treating inflammatory conditions which comprises administering an effective amount of a compound of the formula (A) or pharmaceutically acceptable base salt thereof, or a pharmaceutical composition as defined above. The term "inflammatory condition" includes arthritis, inflammatory bowel disease, psoriasis, allergic encephalitis, gingivitis, systemic lupus erythematosus, diabetes melitis, gout, septic shock and adult respiratory distress syndrome.

The present invention also claims the intermediate compounds, shown below, necessary for synthesizing the compounds of formula (A):

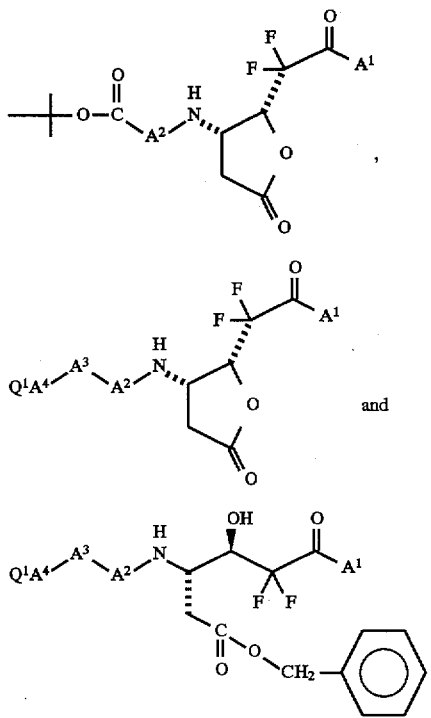

wherein $A^1$, $A^2$, $A^3$, $A^4$ and $Q^1$ are as previously defined.

DETAILED DESCRIPTION OF THE INVENTION

The compounds of the present invention, having the formula (A) as defined above, are readily and generally prepared by the general method described below. Scheme I illustrates the reaction sequence that is followed to generate the compounds of the instant invention. The definitions of $a^1$, $a^2$, $a^3$ and $a^4$ are as follows: $a^1$ is L-Pro- $NR^1R^2$ or —$NR^1R^2$; $a^2$ is N-benzyloxymethyl-L-His, S-benzyl-L-Cys, L-Cys(Me), L-Phe, L- Phe-$R^3$, L-Val, L-Ala, L-Ile, L-Leu or O-benzyl-L-Tyr; $a^3$ is L-Val, L-Leu, L-Ile, O-benzyl-L- Tyr, L-Phe or L-Phe-$R^3$; and $a^4$ is L-Phe, L-Phe-$R^3$, O-benzyl-L-Tyr or L-Leu. $R^1$, $R^2$, $R^3$ and $Q^1$ are as defined hereinabove. The compounds of formula (I) and (II) have the following general structures:

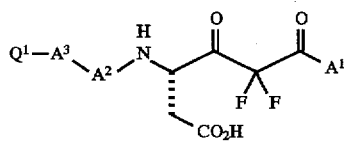

(I)

and

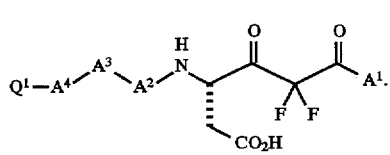

(II)

Scheme 1

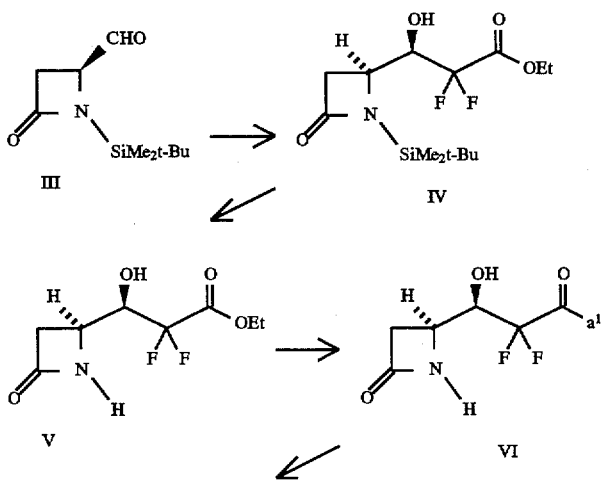

-continued
Scheme 1

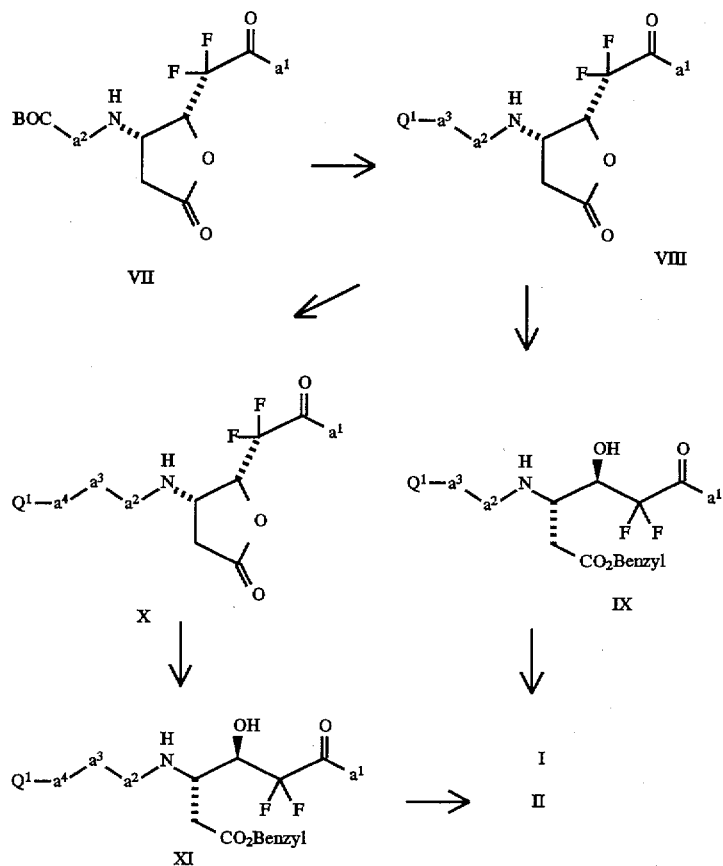

The starting material is the known enantiomerically pure aldehyde, (2S)-1-[(1,1-dimethylethyl)dimethylsilyl]-4-oxo-2-azetidinecarboxaldehyde (III) prepared according to the procedure of Labia and Morin (*Chem. Lett.* 1984, 1007). In the first step, III is reacted with $BrZnCF_2CO_2Et$ to give a mixture of the alcohol IV (ethyl [R-(R*,S*)]-1-[(1,1-dimethylethyl)dimethylsilyl]-α,α-difluoro-β-hydroxy-4-oxo-2-azetidinepropanoate) and its Cβ epimer (ethyl [S-(S*, S*)]-1-[(1,1-dimethylethyl)dimethylsilyl]-α,α-difluoro-β-hydroxy-4-oxo-2-azetidinepropanoate). The reaction is typically carried out in tetrahydrofuran as solvent although other ether solvents such as diethyl ether and 1,2-dimethoxyethane can be used. The $BrZnCF_2CO_2Et$ is normally formed in situ by reaction of ethyl bromodifluoroacetate with zinc powder (activated by washing with dilute mineral acid and drying). The formation of $BrZnCF_2CO_2Et$ can be accelerated greatly by ultrasound irradiation either by carrying out the reaction in an ultrasound bath or by the use of an emersed ultrasound probe. Thus the reaction is normally carried out by dissolving III (about 1 equivalent) and ethyl bromodifluoroacetate (about 1.1 to 10 equivalents, typically 2 equivalents) in the reaction solvent, adding Zn powder (about 2 to 100 equivalents, typically 3 equivalents) and immersing the reaction vessel in an ultrasound bath. The reaction temperature using ultrasound can vary between about 0° C. and the boiling point of the solvent (provided this is less than 100° C.). A reaction temperature of approximately 35° C. is normally used with ultrasound irradiation; under these conditions the reaction time is about 1 hour although shorter (10 minutes) or longer reaction times (12 hours) can be used. The reaction may alternatively be carried out without ultrasonic irradiation. Under these conditions, higher reaction temperatures may be required although the upper limit for temperature still applies (100° C.). Another means of carrying out the reaction is to pre-form the $BrZnCF_2CO_2Et$ by the reaction of zinc powder (about 3 equivalents) with ethyl bromodifluoroacetate (about 3 equivalents) and iodine (about 0.05 equivalents) in an ether solvent (for example tetrahydrofuran, diethyl ether, or 1,2-dimethoxyethane) using heat or ultrasound (Altenburger and Schirlin, *Tetrahedron Letters* 1991, 32, 7255). After formation of the organozinc reagent, a solution of III, dissolved in the same solvent being used for the reaction, is added dropwise and when addition is complete, ultrasonication or heating is continued for up to about 12 hours. Yet another procedure is to add a solution of III and ethyl bromodifluoroacetate (about 10 equivalents) in an ether solvent (for example tetrahydrofuran, diethyl ether, or 1,2-dimethoxyethane) to the preformed low-valent titanium species formed by the reaction of zinc powder (about 1 equivalent) with titanium tetrachloride (about 0.6 equivalents) (Parris et al, *Biochemistry*, 1992, in press) in the same solvent. Regardless of the manner in which the reaction is carried out, the workup is the same. The reaction is poured into water or a saturated aqueous solution of ammonium chloride and extracted with an immiscible organic solvent preferably diethyl ether or ethyl acetate. After drying, evaporation of the solvent leaves the crude mixture of products. The desired product IV is isolated by flash chromatography on silica gel eluting with 3:7 ethyl acetate/hexane; the more polar Cβ epimer is eluted after IV.

The next step involves the removal of the t-butyldimethylsilyl (TBDMS) protecting group from the β-lactam nitrogen. This reaction is normally carried out by treatment of a solution of IV in acetonitrile with an excess of HF/pyridine complex. Reaction temperatures between −20° C. and 50° C. are acceptable, with about 0° C. being preferred. At this temperature the reaction time is about 1.5 hours although reaction times may vary between 10 minutes and 12 hours. The reaction is typically worked up by dilution with water and repeated extraction with ethyl acetate. After drying and removal of solvent, the crude product V remains and is typically of sufficient purity for use in the next step. Other procedures well precedented in the literature may also be applicable to carrying out this reaction, for example HCl in methanol/water (Salzmann et al. *J. Am. Chem. Soc.*, 1980, 102, 6161).

The ethyl ester V is subsequently converted to the corresponding amide VI. For the formation of amides derived from primary and secondary amines ($a^1=NR^1R^2$), the conversion is carried out by direct reaction between V (about 1 equivalent) and the amine $HNR^1R^2$ (1 to 20 equivalents, typically 2 equivalents). The preferred solvent for the reaction is methylene chloride although many other solvents including toluene, chloroform, ethanol, N,N-dimethylformamide, and ethyl acetate may be used. Reaction temperatures vary between about 0° C. and 80° C.; at higher temperatures unwanted side-reactions involving attack by the amine on the β-lactam may occur. The usual reaction temperature in methylene chloride is about 20° C.; and the reaction time is typically about 1.5 hours, although the time can be varied from 1 hour to 1 day. Workup of the reaction is normally carried out by evaporating the solvent followed by flash chromatography on silica gel or diluting with ethyl acetate, washing with dilute mineral acid and evaporating the solvent. For the formation of L-proline amides VI ($a^1$=L-ProNR$^1$R$^2$), amide bond formation is carried out by prior hydrolysis of the ethyl ester group to give the corresponding carboxylic acid followed by coupling with the appropriate L-proline derivative (H-L-ProNR$^1$R$^2$). The hydrolysis step is carried out by the action of MOH (1 to 1.5 equivalents, typically about 1.1 equivalents; M=Na, K, or Li) in a 1:10 mixture of $H_2O$ and tetrahydrofuran at about 0° C. followed by neutralizing with aqueous mineral acid, extracting with ethyl acetate, and removal of solvent. Numerous methods exist which can be used in the subsequent amide bond forming step; these are well detailed in the literature and include coupling with bis(2-oxo-3-oxazolidinyl)phosphinic chloride (Rich et al., *J. Org. Chem.*, 1990, 55, 2895), diethylphosphoryl cyanide (Yamada et al., *Tetrahedron Lett.*, 1973, 14, 1595), N-ethoxycarbonyl-2-ethoxy-1,2-dihydroquinoline (Belleau and Malek, *J. Am. Chem. Soc.*, 1968, 90, 1651), dicyclohexylcarbodiimide (Konig and Geiger *Ber.*, 1970, 103, 788) and mixed anhydride formation (Vaughn and Osato *J. Am. Chem. Soc.*, 1951, 73, 5553).

The next step involves coupling of the intermediate VI (about 1 equivalent) with an N-t-butoxycarbonyl α-amino acid N-hydroxysuccinimide ester (1 to 10 equivalents, typically about 1.1 equivalents) with accompanying β-lactam ring opening and lactonization to give VII. The reaction is carried out in the presence of a tertiary amine base (1 to 10 equivalents, typically about 2 equivalents) such as triethylamine or diisopropylethylamine. An inert solvent such as chloroform, toluene, ethyl acetate or methylene chloride (preferably methylene chloride) is used. Reaction temperatures from 0° C. to 80° C. can be used depending on the solvent. The normal temperature used in methylene chloride is about 20° C., and the reaction time is typically about 18 hours, although the time can be varied from 12 hours to 3 days. The product VII is normally isolated by evaporating the solvent followed by flash chromatography on silica gel.

Peptide chain extension reactions analogous to the formation of lactone VIII from VII are described in the literature and are well known to those skilled in the art of peptide synthesis. The N-t-butoxycarbonyl protecting group is first removed by treating a solution of VII in methylene chloride with an excess of trifluoroacetic acid (TFA) at about 0° C. The volatile solvent and TFA are removed in vacuo and the intermediate TFA amine salt is coupled to an amino acid derivative of structure BOC-$a^3$-OH, BOC-$a^3$- OX, Z-$a^3$—OH or Z-$a^3$—OX (where BOC is t-butoxycarbonyl, Z is benzyloxycarbonyl, X is N-succinimidyl or pentafluorophenyl) in the presence of a tertiary amine base (e.g. triethylamine or diisopropylethylamine) to give VIII ($Q^1$ is t-butoxycarbonyl or benzyloxycarbonyl). The preferred solvent for the coupling step is methylene chloride, although other solvents, e.g. chloroform or N,N-dimethylformamide can be used.

For the preparation of compounds of formula I, ($Q^1$ is t-butoxycarbonyl or benzyloxycarbonyl), an intermediate VIII ($Q^1$ is t-butoxycarbonyl or benzyloxycarbonyl) is next converted to a benzyl ester IX ($Q^1$ is t-butoxycarbonyl or benzyloxycarbonyl). This is accomplished by hydrolyzing the lactone function by treating VIII ($Q^1$ is t-butoxycarbonyl or benzyloxycarbonyl) with MOH (1 to 1.5 equivalents, preferably about 1.1 equivalents; M is Na, K, or Li, preferably Li) in a 1:5 mixture of $H_2O$ and tetrahydrofuran at 20° C. The time for this reaction is typically about 2 hours. The solvents are evaporated to leave the metal salt of the corresponding γ-hydroxyester as a solid which is dried under vacuum. The salt is dissolved in dry N,N-dimethylformamide and the resulting solution is treated with benzyl bromide (1 to 10 equivalents, preferably about 1.5 equivalents). The solution is stirred for 1 to 12 hours (typically 5 hours) at about 20° C. and is then poured into water. Other reaction temperatures between 0° C. and 80° C. can be used. The mixture is extracted with ethyl acetate and the combined ethyl acetate fractions are dried and concentrated to leave the crude product mixture. The intermediate IX ($Q^1$ is t-butoxycarbonyl or benzyloxycarbonyl) is then purified by flash chromatography of the mixture on silica gel, typically using ethyl acetate or some combination of ethyl acetate and hexane as eluant.

For the preparation of compounds of formula I, ($Q^1$ is $R^1CO$ or PhCO), an intermediate VIII ($Q^1$ is t-butoxycarbonyl) is treated with trifluoroacetic acid (TFA) as in the conversion of VII to VIII. The resulting TFA salt of the corresponding amino compound is then treated with an acid chloride of the formula $R^1COCl$ or PhCOCl or an anhydride of the formula $(R^1CO)_2O$ or $(PhCO)_2O$ in the presence of a tertiary amine such as triethylamine to give VIII ($Q^1$ is $R^1CO$ or PhCO). This is subsequently transformed into IX ($Q^1$ is $R^1CO$ or PhCO) by the same procedure as for the conversion of VIII ($Q^1$ is t-butoxycarbonyl or benzyloxycarbonyl) to IX ($Q^1$ is t-butoxycarbonyl or benzyloxycarbonyl).

The final reaction sequence to provide compounds of formula I is as follows. The alcohol function of an intermediate IX is first oxidized to the ketone using 1,1,1-triacetoxy-1,1-dihydro-1,2-benziodoxol-3(1 H)-one according to the procedure described by Linderman (*Tetrahedron Lett.*, 1987, 28, 4259). Next, the benzyl ester function is cleaved to give I by catalytic hydrogenolysis using palladium on charcoal. The preferred solvent for the hydrogenolysis is ethanol although other solvents such as ethyl acetate or acetic acid may be used. The preferred pressure of hydrogen is about 3 atmospheres although the range may vary between 1 and 50 atmospheres. The reaction temperature is typically about 20° C. The product I is isolated by filtration to remove the catalyst followed by evaporation of solvent. For the preparation of compounds of formula I where $Q^1$ is benzyloxycarbonyl, it is often preferable to hydrolyze the benzyl ester by treatment of IX ($Q^1$ is benzyloxycarbonyl) with MOH (1 to 1.5 equivalents, preferably about 1.1 equivalents; M=Na, K, or Li, preferably Li) in a 1:5 mixture of $H_2O$ and tetrahydrofuran at about 20° C. The compound of formula I ($Q^1$ is benzyloxycarbonyl) is then isolated by neutralization of the reaction mixture with mineral acid, extraction with ethyl acetate, removal of solvent and chromatography on silica gel.

To synthesize compounds of formula II, an intermediate VIII ($Q^1$ is t-butoxycarbonyl) is extended to an intermediate X ($Q^1$ is t-butoxycarbonyl or benzyloxycarbonyl) by the same procedure used in the conversion of VII to VIII ($Q^1$ is t-butoxycarbonyl or benzyloxycarbonyl) using BOC-$a^4$—OH, BOC-$a^4$—OX, Z-$a^4$—OH or Z-$a^4$- OX (where BOC is t-butoxycarbonyl, Z is benzyloxycarbonyl, X is N-succinimidyl or pentafluorophenyl). For the synthesis of compounds of formula II ($Q^1$ is $R^1$CO or PhCO), an intermediate X ($Q^1$ is t-butoxycarbonyl) is treated with trifluoroacetic acid (TFA). The resulting TFA salt of the corresponding amino compound is then treated with an acid chloride of the formula $R^1$COCl or PhCOCl or an anhydride of the formula $(R^1CO)_2O$ or $(PhCO)_2O$ in the presence of a tertiary amine such as triethylamine to give X ($Q^1$ is $R^1$CO or PhCO). The final conversions of X to XI and then to II are carried out as described for the sequence VIII to IX to I. For the preparation of compounds of formula II where $Q^1$ is benzyloxycarbonyl, it is often preferable to cleave the benzyl ester by treatment of XI with MOH as for the synthesis of compounds of formula I ($Q^1$ is benzyloxycarbonyl).

Compounds where $a^2$ is L-His or L-Cys, L-Tyr, and/or $a^4$ is L-Tyr require side chain protection. These amino acids are introduced with the following side chain protecting groups: L-His, N-benzyloxymethyl; L-Cys, S-benzyl; L-Tyr, O-benzyl. With L-His the side chain protecting group is removed during the final hydrogenolysis of the benzyl ester giving I or II. If $Q^1$ is benzyloxycarbonyl, loss of this group may occur necessitating treatment of the product with benzyl chloroformate to re-introduce the benzyloxycarbonyl group. If L-Cys and/or L-Tyr are introduced, the benzyl side chain protecting groups of these amino acids are removed from the intermediates IX or XI by treatment with neat HF. These conditions also serve to cleave the benzyl ester, the N-benzyloxymethyl on L-His (if present), and/or the benzyloxycarbonyl group at $Q^1$ (if present) or the t-butoxycarbonyl group at $Q^1$ (if present). If the $Q^1$ group is lost, i.e. when $Q^1$ is t-butoxycarbonyl or benzyloxycarbonyl, the group may be re-introduced by treatment with di-t-butyldicarbonate or benzyl chloroformate respectively.

The ability of the compounds of this invention to inhibit interleukin 1β converting enzyme (ICE) and, consequently, demonstrate the compounds' effectiveness for treating inflammatory diseases is shown by the following in vitro assay. Other procedures for purification and assaying (ICE) are shown in Black et al., *Febs Letters*, 247 2, pp. 386–390, 1989, and Thornberry et al., *Nature*, 356, pp. 768–774, 1992.

Cell culture and lysates. Human monocyte cell line, THP-1 (ATCC-TIB 202) is grown in RPMI media 1640 (Gibco BRL Gaithersburg, Md. 20877) with 10% fetal bovine serum, harvested by centrifugation, washed twice in Dulbecco's PBS dithiothreitol without $Ca^{++}$ ethylene aliamine tetraacetic acid and $Mg^{++}$, and resuspended in buffer (10 mM Tris-HCl pH 7.8, 5 mM DTT (dithiothreitol), 1 mM EDTA, 1 mM PMSF (phenylmethyl sulfonyl fluoride), 1 μg/ml pepstatin, and 1 μg/ml leupeptin) at $1–3\times10^8$ cells per ml. Cells are frozen at –70° C. until use and then lysed by thawing. Lysates are cleared by centrifugation at 20,000×g for 1 hour followed by 120,000×g for 1 hour.

Partial purification of ICE activity by ion-exchange chromatography. ICE activity is purified from THP-1 cell lysates by three steps of ion exchange chromatography. (A) THP-1 cell lysate (1.5 L) is chromatographed by ion-exchange on Q-Sepharose Fast Flow (Pharmacia LKB Biotechnology Piscataway, N.J. 08854) in buffer A (20 mM Tris pH 7.8, 5 mM EDTA, 1 mM PMSF, 1 μg/ml pepstatin, and 1 μg/ml leupeptin). ICE activity is eluted with a gradient of NaCl in buffer A. (B) The active pool from A is chromatographed by anion exchange on MonoQ monobeads (Pharmacia LKB Biotechnology Piscataway, N.J. 08854) in buffer A and activity eluted in a NaCl gradient. (C) The active pool from B is chromatographed by cation exchange on monoS monobeads (Pharmacia LKB Biotechnology Piscataway, N.J. 08854) in buffer B (25 mM NaMES (2-[N-morpholino] ethanesulfonic acid, hemisodium salt) pH 6.9, 5 mM DTT, 1 mM EDTA, 10% glycerol, 1 mM PMSF, 1 μg/ml pepstatin, and 1 μg/ml leupeptin). Activity is eluted in a NaCl gradient. The active pool from C is used in the subsequent assay to measure the ICE inhibitory activity of the compounds comprising this invention.

ICE Assay. ICE activity is assayed by combining 10 μl partially purified enzyme fraction containing 10 mM Tris-HCl (pH 7.8) with protease inhibitors (1 mM PMSF, 1 μg/ml pepstatin, and 1 μg/ml leupeptin), with test compound in a 40 μl volume (yielding a 20% DMSO concentration after substrate is added). The reaction is initiated by the introduction of [$^{35}$S]-metabolically labelled human peripheral blood monocyte proteins (containing [$^{35}$S] labelled pro-IL-1β substrate) in a total volume of 50 μl and terminated 10 minutes later by the addition of 10 μl of 0.9M NaCl. The cleaved and uncleaved forms of IL-1β are immunocaptured by the addition of 5 μl of polyclonal anti-IL-1β antibody (Cistron Biotechnology, Box 2004, 10 Bloomfield Avenue, Pine Brook, N.J. 07058, product #02-1100) in 50 μl PBS (Dulbecco's Phosphate Buffered Saline) (pH 8) plus 0.1% SDS (Sodium Dodecyl Sulfate Detergent), 0.1% Triton X-100 (Nonionic detergent Sigma Chemical Co., P.O. Box 14508, St. Louis, Mo. 63178), 0.1% Nonidet P40 (NP-40, Nonionic Detergent Sigma Chemical Co., P.O. Box 14508, St. Louis, Mo. 63178) and further incubation for 4 hours at 4° C. Immune complexes are insolubilized by the addition of 25 μl of a 50% slurry of Protein-A Sepharose, and incubation overnight at 4° C. The insolubilized complexes are recovered by centrifugation (Eppendorf microfuge), and washed three times using a 10× volume of PBS (pH 8) with 0.1% Triton X-100, 0.1% SDS, 0.1% NP-40. After the last wash, a volume of 25 μl containing 2% SDS, 200 mM dithiothreitol in 0.125M Tris buffer (pH 6.8) (2× Laemmli sample buffer [0.125M Tris-HCl pH 6.8, 4% SDS, 20% Glycerol, 10% 2-mercaptoethanol, 0.002% Bromophenol Blue]) with 20% glycerol are added to the pellet. The immune complexes are released from the Protein A and the [IL1-anti-IL1] complexes dissociated by immersing the tubes in boiling water. Two minutes later, the tubes are chilled in ice, and centrifuged to pellet the protein A Sepharose.

After clarification by centrifugation, a 25 μl aliquot is applied to a 10–20% gradient of Laemmli SDS PAGE (Integrated Separation Systems, One Westinghouse Plaza, Hyde Park, Mass. 02136) and electrophoresed at 50 mA per gel for approximately 75 minutes. After removal, the gels are fixed in 10% HOAc:30% MeOH for 60 minutes at ambient, and bathed in AMPLIFY (Amersham Co., Arlington Heights, Ill. 60005) for 30 minutes at ambient. The gels are then dried on a vacuum drier (Hoeffer) for 90 minutes at 60° C., and developed using Kodak XAR film (Parker X-Ray, 260 Governor Street, E. Hartford, Conn. 06108) at −70° C.

Bands corresponding to pro- and mature forms of IL-1β are quantitated by elution using 0.5 ml of 0.1M Tris (pH 8), 20 mM $CaCl_2$, and 10 mg/ml pronase incubated at 56° for 4 hours. After the addition of 4 ml of Ready-Safe (Liquid Scintillation Cocktail) (Beckman Instruments Inc., Fullerton, Calif. 92034), the digests are counted using a liquid scintillation counter.

The pharmaceutically acceptable base salts of the compounds of the formula (A) are those formed from bases which form non-toxic base salts, for example the sodium, potassium and ammonium salts.

For administration to humans in the curative or prophylactic treatment of inflammatory conditions using a compound of formula (A) above, oral dosages of the compounds are generally in the range from 2–100 mg daily for an average adult patient (70 kg). Thus for a typical adult patient, individual tablets or capsules containing from 1 to 10 mg of active compound, in a suitable pharmaceutically acceptable vehicle or carrier, are used. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (A) can be administered alone, but will generally be administered in an admixture with a pharmaceutical carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

The present invention is illustrated by the following examples, but it is not limited to the details thereof.

EXAMPLE 1

[S]-N-[(1,1-Dimethylethoxy)carbonyl-L-Valyl-N-[3, 3-Difluoro-2,4-Dioxo-1-Carboxymethyl-4-(1-Pyrrolidinyl)Butyl]-L-Alaninimide A. Ethyl [S-(S*,S*)]-1-[(1,1-dimethylethyl) dimethylsilyl]-α,α-difluoro-β-hydroxy-4-oxo-2-azetidinepropanoate and ethyl [R-(R*,S*)]-1-[(1,1-dimethylethyl)dimethylsilyl]-α,α-difluoro-β-hydroxy-4-oxo-2-azetidinepropanoate To a solution of freshly prepared crude (2S)-1-[(1,1-dimethylethyl)dimethylsilyl]-4-oxo-2-azetidinecarboxaldehyde (10.3 g, 48.3 mmol) and ethyl bromodifluoroacetate (25.0 g, 123 mmol) in THF (100 ml) was added Zn powder (10.5 g, 161 mmol). The reaction flask was placed in a sonicating bath at 35° C. for 40 minutes with occasional manual agitation. The mixture was then poured into ice/$H_2O$ and the resulting slurry was filtered through celite, washing well with ether. The aqueous layer was separated and extracted with ether. The mixture was chromatographed on silica gel using 3:7 ethyl acetate/hexane as eluant. Complete separation of the epimeric products was not achieved. Fractions containing only the less polar product provided a solid which was triturated with hexane leaving pure ethyl [R-(R*,S*)]-1-[(1,1-dimethylethyl) dimethylsilyl]-α,α-difluoro-β-hydroxy-4-oxo-2-azetidinepropanoate as white crystals (5.17 g, 31.5%), m.p. 91°–93° C., $[\alpha]^{20}_D$−10.6° (c 1.13, $CHCl_3$), $v_{max}$ 3578, 1747 $cm^{-1}$. MS(FAB): m/z 338. Elemental Anal. Calc'd for $C_{14}H_{25}F_2NO_4Si$: C, 49.83; H, 7.47; N, 4.12. Found: C, 49.90; H, 7.28; N, 4.15.

Fractions containing only the more polar product provided a solid which was triturated with hexane leaving pure ethyl [S-(S*,S*)]-1-[(1,1-dimethylethyl)dimethylsilyl]-α,α-difluoro-β-hydroxy-4-oxo-2-azetidinepropanoate as white crystals (1.26 g, 7.7%), mp 101°–103° C., $[\alpha]^{20}_D$−54.8° (c 1.70, $CHCl_3$), $v_{max}$ 3669, 1738 $cm^{-1}$. MS (FAB): m/z 338. Elemental Anal. Calc'd for $C_{14}H_{25}F_2NO_4Si$: C, 49.83; H, 7.47; N, 4.12. Found: C, 49.93; H, 7.39; N, 4.15.

B. [R-(R*,S*)]-α,α-Difluoro-β-hydroxy-4-oxo-2-azetidinepropanoate

To a solution of [R-(R*,S*)]-1-[(1,1-dimethylethyl) dimethylsilyl]-α,α-difluoro-β-hydroxy-4-oxo-2-azetidinepropanoate (1.0 g, 2.96 mmol) in $CH_3CN$ (20 ml) at 0° C. was added HF/pyridine (1 ml). After stirring for 40 minutes at 0° C., more HF/pyridine (1 ml) was added; stirring was continued for an additional 30 minutes. The mixture was diluted with $H_2O$ and then extracted with ethyl acetate (3×). The combined ethyl acetate extracts were dried and concentrated to afford [R-(R*,S*)]-α,α-difluoro-β-hydroxy-4-oxo-2-azetidinepropanoate as a pale orange oil (667 mg, 100%). [1] HNMR: 1.32 (t, 3 H, J=7.1 Hz, $CH_2Me$), 2.90 (br d, 1 H, J=15.0 Hz, CHCON), 3.07 (ddd, J=1.5, 4.9, 15.0 Hz, CHCON), 3.98 (e, 1 H, $CHCH_2$), 4.09 (dt, 1 H, J=5.0, 18 Hz, $CHCF_2$), 4.33 (q, 2 H, J=7.1 Hz, $CH_2Me$), 4.70 (br s, 1 H, OH), 6.99 (br s, 1 H, NH).

C. [R-(R*,S*)]-1-[3-(4-Oxo-2-azetidinyl)-2,2-difluoro-3-hydroxy-1-oxopropyl]pyrrolidine

[R-(R*,S*)]-α,α-Difluoro-β-hydroxy-4-oxo-2-azetidinepropanoate was dissolved in $CH_2Cl_2$ (5 ml). The solution was cooled to 0° C. and pyrrolidine (0.5 ml, 6.0 mmol) was added. m.p. 104°–106° C., $[\alpha]^{20}_D$+10.0° (c 2.08, $CH_2Cl_2$), $v_{max}$ 3416, 1766, 1646 $cm^{-1}$. MS (EI): m/z 249 (M+H[+]). Elemental Anal. Calc'd for $C_{10}H_{14}F_2N_2O_3$: C, 48.39; H, 5.68; N, 11.29. Found: C, 48.51; H, 5.68; N, 11.24.

D. (2R-cis)-N-[(1,1-Dimethylethoxy)carbonyl]-N-[2-[1, 1-difluoro-2-oxo-2-(1-pyrrolidinyl)ethyl]tetrahydro-5-oxo-3-furanyl]-L-alaninimide To a solution of [R-(R*,S*)]-1-[3-(4-oxo-2-azetidinyl)-2, 2-difluoro-3-hydroxy-1-oxopropyl]-pyrrolidine (158 mg, 0.637 mmol) and triethylamine (0.18 ml, 1.29 mmol) in $CH_2Cl_2$ (4 ml) at 25° C. was added N-(tert-butoxycarbonyl)-L-alanine N-hydroxysuccinimide ester (200 mg, 0.698 mmol). The mixture was stirred at 25° C. for 18 hours and then concentrated to leave an oil. This was chromatographed on silica gel eluting with 3:1 ethyl acetate/hexane as eluant. Fractions containing only (2R-cis)-N-[(1,1-dimethylethoxy)carbonyl]-N-[2-[1,1-difluoro-2-oxo-2-(1-pyrrolidinyl)ethyl]

tetrahydro-5-oxo-3-furanyl]-L-alaninimide yielded an oil (175 mg, 66%), [α]$^{20}_D$ –45.9° (c 3.50, CH$_2$Cl$_2$), v$_{max}$ 3428, 3324, 1802, 1693, 1650 cm$^{-1}$. MS (FAB): m/z 420.

E. (2R-cis)-N-[(1,1-Dimethylethoxy)carbonyl]-L-valyl-N-[2-[1,1-difluoro-2-oxo-2-(1-pyrrolidinyl)ethyl] tetrahydro-5-oxo-3-furanyl]-L-alaninimide To a solution of (2R-cis)-N-[(1,1-dimethylethoxy)carbonyl]-N-[2-[1,1-difluoro-2-oxo-2-(1-pyrrolidinyl)ethyl] tetrahydro-5-oxo-3-furanyl]-L-alaninimide (260 mg, 0.620 mmol) in CH$_2$Cl$_2$ (4 ml) cooled in an ice bath was slowly added TFA (4 ml). The resulting mixture was stirred for 2 hours at 0° C. at which point the solvents were evaporated to leave an oil. This was dissolved in CH$_2$Cl$_2$ and the solution was cooled in an ice bath. Diisopropylethylamine (0.20 ml, 1.15 mmol) and BOC-L-valine-N-hydroxysuccinimide ester (290 mg, 0.922 mmol) were added sequentially. After stirring for 4 hours at 25° C., the mixture was diluted with ethyl acetate and washed with 1N HCl. The aqueous wash was extracted with ethyl acetate. The combined ethyl acetate fractions were washed with saturated NaHCO$_3$, dried and concentrated to leave an oil which was chromatographed on silica gel eluting with 4:1 ethyl acetate/hexane. Fractions containing only (2R-cis)-N-[(1,1-dimethylethoxy)carbonyl]-L-valyl-N-[2-[1,1-difluoro-2-oxo-2-(1-pyrrolidinyl)ethyl]tetrahydro-5-oxo-3-furanyl]-L-alaninimide yielded an oil, (231 mg, 72%), [α]$^{20}_D$ –47.8° (c 1.38, CHCl$_3$), v$_{max}$ 3416, 3326, 1800, 1702 (sh), 1695, 1656 cm$^{-1}$. High Resolution MS Calc'd for C$_{27}$H$_{37}$F$_2$N$_4$O$_7$: 519.2630. Found: 519.2620.

F. [R-(R*,S*)]-N-[(1,1-Dimethylethoxy)carbonyl]-L-valyl-N-[3,3-difluoro-2-hydroxy-4-oxo-1-[2-oxo-2-(phenylmethoxy)ethyl]-4-(1-pyrrolidinyl)butyl]-L-alaninimide A solution of (2R-cis)-N-[(1,1-dimethylethoxy)carbonyl]-L-valyl-N-[2-[1,1-difluoro-2-oxo-2-(1-pyrrolidinyl)ethyl] tetrahydro-5-oxo-3-furanyl]-L-alaninimide in MeOH (1.5 ml) and THF (1.5 ml) was cooled in an ice bath at 0° C. and aqueous 1.31M LiOH solution (0.25 ml, 0.33 mmol) was added. The mixture was stirred at 0° C. for 1 hour and then at 20° C. for 2 hours until disappearance of starting material was complete as determined by TLC (silica gel, ethyl acetate eluant). After evaporation of the solvents, the residue was dried under vacuum for 18 hours to afford a white solid. This was dissolved in dry DMF (3 ml) and benzyl bromide (0.055 ml, 0.46 mmol) was added. After stirring at room temperature for 4.5 hours, the solution was poured into water and the resulting mixture was extracted with ethyl acetate (3×). The combined ethyl acetate extracts gave a pale yellow oil on drying and evaporation. This was chromatographed on silica gel eluting with 4:1 ethyl acetate/hexane to afford [R-(R*,S*)]-N-[1,1-dimethylethoxy)carbonyl]-L-valyl-N-[3,3-difluoro-2-hydroxy-4-oxo-1-[2-oxo-2-(phenylmethoxy)ethyl]-4-(1-pyrrolidinyl)butyl]-L-alaninimide as a clear oil, (135 mg, 71%), [α]$^{20}_D$ –23.8° (c 1.14, CHCl$_3$), v$_{max}$ 3423, 1728 (sh), 1708 (sh), 1649 cm$^{-1}$. HRMS Calc'd for C$_{30}$H$_{45}$F$_2$N$_4$O$_8$: 627.3208. Found: 627.3151.

G. [S]-N-[(1,1-Dimethylethoxy)carbonyl]-L-valyl-N-[3,3-difluoro-2,4-dioxo-1-[2-oxo-2-(phenylmethoxy)ethyl]-4-(1-pyrrolidinyl)butyl]-L-alaninimide To a solution of [R-(R*,S*)]-N-[(1,1-dimethylethoxy)carbonyl]-L-valyl-N-[3,3-difluoro-2-hydroxy-4-oxo-1-[2-oxo-2-(phenylmethoxy) ethyl]-4-(1-pyrrolidinyl)butyl]-L-alaninimide (129 mg, 0.206 mmol) in CH$_2$Cl$_2$ (5 ml) at 20° C. was added the Dess-Martin reagent (1,1,1-triacetoxy-1,1-dihydro-1,2-benziodoxol-3(1H)-one) (320 mg, 0.75 mmol). The resulting heterogeneous mixture was stirred at 20° C. for 5 hours and was then quenched by addition of ethyl acetate and a solution of sodium thiosulfate (1.2 g) in saturated NaHCO$_3$ solution (10 ml). After stirring for about 15 minutes when all solids had dissolved, the aqueous layer was separated and extracted with ethyl acetate. The combined ethyl acetate layers were dried and evaporated to leave [S]-N-[(1,1-dimethylethoxy)carbonyl]-L-valyl-N-[3,3-difluoro-2,4-dioxo-1-[2-oxo-2-(phenylmethoxy)ethyl]-4-(1-pyrrolidinyl)butyl]-L-alaninimide as a clear oil (126 mg, 98%). Having a high degree of purity by $^1$H NMR, the material was used immediately in the next step. $^1$H NMR: 0.87 (d, 3 H, J=6.8 Hz, CHMe), 0.93 (d, 3 H, J=6.8 Hz, NCHMe), 1.33 (d, 3 H, J=7.0 Hz, NCHMe), 1.42 (s, 9 H, t-Bu), 1.81–2.00 (m, 4 H, 2×CH$_2$N), 2.10 (m, 1 H, CHMe$_2$), 2.97 (ABX m, 2 H, CH$_2$CO$_2$), 3.47 (e, 2 H, 2×CH$_2$CHN), 3.62 (m, 2 H, 2×CH$_2$CHN), 3.95 (m, 1 H, NCHi-Pr), 4.52 (m, 1 H, NCHMe), 5.09 (AB d, 2×1 H, J=12.2 Hz, PhCH$_2$), 5.15–5.28 (m, 2 H, CHCH$_2$, BOCNH), 6.82 (br d, 1 H, J=7.4 Hz, NH), 7.30–7.41 (m, 6 H, Ph, NH). HRMS (FAB) Calc'd for C$_{30}$H$_{43}$F$_2$N$_4$O$_8$: 625.3051. Found: 627.3068.

H. [S]-N-[(1,1-Dimethylethoxy)carbonyl]-L-valyl-N-[3,3-difluoro-2,4-dioxo-1-carboxymethyl-4-(1-pyrrolidinyl) butyl]-L-alaninimide To a solution of [S]-N-[(1,1-dimethylethoxy)carbonyl]-L-valyl-N-[3,3-difluoro-2,4-dioxo-1-[2-oxo-2-(phenylmethoxy)ethyl]-4-(1-pyrrolidinyl)butyl]-L-alaninimide (124 mg, 0.198 mmol) in EtOH (25 ml) was added 10% Pd on charcoal. The mixture was hydrogenated at 3 atmospheres pressure for 5 hours using a Parr shaker. After removal of the catalyst by filtration through celite, the solvent was evaporated. The residue was chromatographed on silica gel using 1:5:54 AcOH/MeOH/CHCl$_3$ as eluant affording [S]-N-[(1,1-dimethylethoxy)carbonyl]-L-valyl-N-[3,3-difluoro-2,4-dioxo-1-carboxymethyl-4-(1-pyrrolidinyl) butyl]-L-alaninimide as a clear oil (103 mg, 97%). v$_{max}$ 3422, 1812, 1684, 1649 cm$^{-1}$. HRMS (FAB) Calc'd for C$_{23}$H$_{37}$F$_2$N$_4$O$_8$ (MH$^+$)=535.2581. Found: 535.2597.

I claim:

1. A compound of the formula

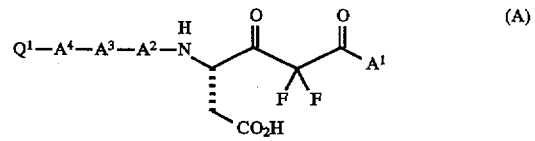

or a pharmaceutically acceptable base salts thereof, wherein A$^1$ is L-Pro-NR$^1$R$^2$ or —NR$^1$R$^2$, where R$^1$ and R$^2$ are independently selected from the group consisting of hydrogen, C$_1$–C$_6$ alkyl and benzyl; or R$^1$ and R$^2$ are taken together with the nitrogen to which they are attached and form

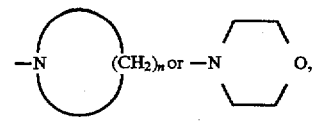

wherein n is an integer from 2 to 6;

A$^2$ is selected from the group consisting of L-His, L-Cys, L-Cys(Me), L-Phe, L-Phe-R$^3$, L-Val, L-Ala, L-Ile, L-Leu and L-Tyr;

A$^3$ is selected from the group consisting of L-Val, L-Leu, L-Ile, L-Tyr, L-Phe and L-Phe- R$^3$;

A$^4$ is selected from the group consisting of a covalent bond, L-Phe, L-Phe-R$^3$, L-Tyr, and L-Leu;

wherein R³ is attached to the aromatic ring of phenylalanine and for each occurrence is selected from the group consisting of C₁–C₆ alkyl, C₁–C₆ alkoxy, benzyl, fluoro, trifluoromethyl and chloro; and Q¹ is selected from the group consisting of t-butoxycarbonyl, benzyloxycarbonyl, R⁴CO and phenylcarbonyl, wherein R⁴ is hydrogen, C₁–C₆ alkyl or benzyl.

2. A compound or a pharmaceutically acceptable base salt thereof according to claim 1 wherein A¹ is —NR¹R² and A⁴ is a covalent bond or L-Tyr.

3. A compound or a pharmaceutically acceptable base salt thereof according to claim 2 wherein A² is L-Phe, L-Val, L-Ala, L-Ile or L-Leu.

4. A compound or a pharmaceutically acceptable base salt thereof according to claim 3 wherein A² is L-Ala and A³ is L-Val.

5. A compound or a pharmaceutically acceptable base salt thereof according to claim 4 wherein Q¹ is t-butoxycarbonyl.

6. A compound or a pharmaceutically acceptable base salt thereof according to claim 5 wherein R¹ and R² are taken together and form

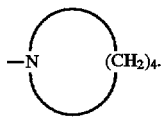

7. A compound or a pharmaceutically acceptable base salt thereof according to claim 6 wherein A⁴ is L-Tyr.

8. A compound or a pharmaceutically acceptable base salt thereof according to claim 6 wherein A⁴ is a covalent bond.

9. A compound of the formula

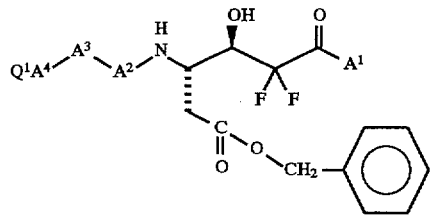

wherein A¹ is L-Pro-NR¹R² or —NR¹R², where R¹ and R² are independently selected from the group consisting of hydrogen, C₁–C₆ alkyl and benzyl; or R¹ and R² are taken together with the nitrogen to which they are attached and form

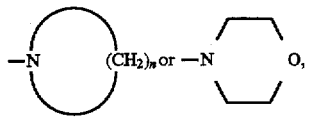

wherein n is an integer from 2 to 6;

A² is selected from the group consisting of L-His, L-Cys, L-Cys(Me), L-Phe, L-Phe-R³, L-Val, L-Ala, L-Ile, L-Leu and L-Tyr;

A³ is selected from the group consisting of L-Val, L-Leu, L-Ile, L-Tyr, L-Phe and L-Phe- R³;

A⁴ is selected from the group consisting of a covalent bond, L-Phe, L-Phe-R³, L-Tyr, and L-Leu;

wherein R³ is attached to the aromatic ring of the phenylalanine and for each occurrence is selected from the group consisting of C₁–C₆ alkyl, C₁–C₆ alkoxy, benzyl, fluoro, trifluoromethyl and chloro; and Q¹ is selected from the group consisting of t-butoxycarbonyl, benzyloxycarbonyl, R⁴CO and phenylcarbonyl, wherein R⁴ is hydrogen, C₁–C₆ alkyl or benzyl.

10. A pharmaceutical composition comprising an amount of a compound or a pharmaceutically acceptable base salt thereof according to claim 1 and a pharmaceutically acceptable diluent or carrier.

11. A method of inhibiting interleukin 1β converting enzyme (ICE) in a mammal in need thereof which comprises administering to said mammal an interleukin 1β converting enzyme inhibiting amount of a compound or a pharmaceutically acceptable base salt thereof according to claim 1.

12. A method of treating an antiinflammatory condition in a mammal which comprises administering to said mammal an antiinflammatory amount of a compound or a pharmaceutically acceptable base salt thereof according to claim 1.

* * * * *